United States Patent [19]

Asano et al.

[11] 3,951,600
[45] Apr. 20, 1976

[54] ACRYLAMIDE AQUEOUS SOLUTION HANDLING METHOD

[76] Inventors: Shiro Asano, No. 1071-2, Nakano-cho, Totsuka, Yokohama, Kanagawa; Kiyotaka Yoshimura, No. 266-9, Takashi, Mobara, Chiba; Ryoji Tsuchiya, No. 15-22, Daimachi 4-chome, Kamakura, Kanagawa; Tadatoshi Honda, No. 1541, Yabe-cho, Totsuka, Yokohama, Kanagawa, all of Japan

[22] Filed: Dec. 4, 1972

[21] Appl. No.: 311,900

[30] Foreign Application Priority Data
Dec. 6, 1971    Japan................................. 46-97894

[52] U.S. Cl..................................... 21/2; 21/60.5 A; 206/84; 220/65; 260/561 N; 526/62; 526/77; 526/90; 526/201; 526/303
[51] Int. Cl.²................. A61L 13/00; C07C 103/08
[58] Field of Search........... 260/561 N, 84; 215/1 C; 252/399, 404; 21/2

[56] References Cited
UNITED STATES PATENTS

| | | | |
|---|---|---|---|
| 2,914,169 | 11/1959 | Moore | 260/84 |
| 2,982,396 | 5/1961 | Shihadeh | 260/84 |
| 3,598,269 | 8/1971 | Carmen | 215/1 |
| 3,615,710 | 10/1971 | Lee | 215/1 C X |
| 3,670,020 | 6/1972 | Moore | 260/561 N |
| 3,671,607 | 6/1972 | Lee | 215/1 C X |
| 3,720,340 | 3/1973 | Lee | 215/1 C |
| 3,758,578 | 9/1973 | Habermann et al. | 260/561 N |

*Primary Examiner*—Ethel G. Love

[57] ABSTRACT

There is disclosed a method for handling acrylamide aqueous solutions with safety wherein acrylamide aqueous solutions obtained through catalytic hydration reaction of acrylonitrile are handled using utensils made from phenol resin, polyethylene, polypropylene, polyvinylchloride resin or fluorine-containing resin or glass or using such utensils that are provided with linings formed by these materials.

4 Claims, No Drawings

ACRYLAMIDE AQUEOUS SOLUTION HANDLING METHOD

BACKGROUND OF THE INVENTION

For the industrial manufacture of acrylamide, there are known some relatively new processes whereby acrylamide aqueous solutions are directly obtained from the catalytic hydration reaction of acrylonitrile. Such processes include, for example, a process disclosed by U.S. Pat. No. 3,381,034 employing copper ion; a process disclosed by U.S. Pat. No. 3,631,104 employing copper oxide, copper-chrome oxide, copper-molybdenum oxide or a copper catalyst obtained by reducing them; and a process disclosed by U.S. Pat. No. 3,674,848 employing a copper salt of acid cation resin, etc. In addition to them, there is another process employing such catalysts as Raney copper, Ulmann copper, reduced copper, copper with a carrier etc. (U.S. Pat. Application Ser. No. 56,967, filed July 21, 1970, owned by the assignee of the patent application).

When the acrylamide aqueous solutions prepared in accordance with such processes are further treated through some refining processes, they become acrylamide monomer aqueous solutions of sufficient purity permitting their use, without further process, for paper processing or agglomerating purposes. While it has some advantages for a commercially available products to be in the form of aqueous solution, there are some problems in handling acrylamide aqueous solutions, such as preventing their deterioration in transit or in storage.

This is a new problem and has not been experienced with the conventional sulfuric acid process for the industrial production of acrylamide wherein acrylamide is obtained in a crystallized form by removing by-product ammonium sulfate. The problem still remains unsolved.

The problem in connection with the handling of the acrylamide aqueous solutions that are prepared by catalytic hydration processes arises from the polymerization of acrylamide which is readily polymerized causing deterioration of the products in transit or in storage over a long period of time. As a generally applicable method, it is often adopted in handling readily-polymerizing materials to cause a suitable quantity of a proper polymerization inhibitor to coexist in the solution of such a matter. However, in cases where an acrylamide aqueous solution is polymerized for direct use as an acrylamide prepolymer solution, such concomitant polymerization inhibitor hinders normal polymerization reaction, and then the stable reinforcement of paper or stable agglomeration of effluent treatment cannot be attained as desired.

OBJECT OF THE INVENTION

An object of this invention is to provide a method for safe handling of acrylamide aqueous solution preventing the polymerization of acrylamide that ends to be polymerized in transit or in storage over a long period of time, without the use of the inhibitor conventionally used against the polymerization of acrylamide.

Another object of this invention is to provide a high purity acrylamide aqueous solution which remains unchanged in hue and in pH value and does not become turbid in transit or during a long period of storage.

SUMMARY OF THE INVENTION

In accordance with this invention, the acrylamide aqueous solution that is obtained by subjecting acrylonitrile to a catalytic hydration process is handled using utensils made of resins such as phenol resin, polyethylene, polypropylene, fluorine contained resin and polyvinylchloride resin or glass or using such utensils that are provided with linings made of such materials. By this, for example, the polymerization of acrylamide which tends to take place during transportation or long period storage can be prevented, so that it can be handled with safety without causing contamination by the addition of a polymerization inhibitor.

The method of the invention makes it possible to use a high purity acrylamide aqueous solution which is free from changes in hue and in pH value and never becomes turbid in transit or during a long period of storage.

DETAILED DESCRIPTION OF THE INVENTION

Materials for the utensils, storage containers for example, that can be employed in handling the acrylamide aqueous solutions obtained by catalytic hydration processes must meet the following prerequisites:

1. Material never deteriorates itself nor decreases in measurements.
2. Material never colors the aqueous solution nor causes turbidity.
3. In addition to these prerequisites, such materials must not cause polymerization of the aqueous solution.

For example, although stainless steel SUS-27 completely satisfies the condition (2) above, it does not meet the condition (3) when used as a container over a long storage period. It is difficult to perceive the mechanism of the polymerization of the aqueous solution. Accordingly it is also quite difficult to select a material that never causes such polymerization.

It is a further requirement in terms of, for example, temperature in transporting acrylamide aqueous solutions that such materials must be usable at temperatures ranging from −10° to 60°C taking into consideration unusual conditions to be encountered in transit, such as temperature in a cold climate, or temperature around a heater when a storage container is equipped with such for the purpose of preventing a concentrated solution from crystallizing.

The method of the invention for handling acrylamide aqueous solutions not only meets the above stated requirements but also never accelerates the polymerizing of acrylamide. This invention can be practiced without difficulty by just using utensils made of such resins as phenol resin, polyethylene, polypropylene, fluorine containing resin, polyvinylchloride resin etc. or made of glass or by using utensils that are provided with linings formed by such materials. The shapes of such utensils include reservoirs for the storage of products and containers for use in transit. The shapes of such utensils may also include piping tubes and reservoirs for manufacturing processes and other items that are required in the processes of handling acrylamide aqueous solutions such as an acrylamide crystallizing process.

The examples of suitable utensils made of such resins or glass include containers with phenol resin linings, utensils or containers made of or provided with linings made of low- or high-density polyethylene; utensils or containers made of or provided with linings of polypropylene, for example containers or utensils composed or provided with linings of fluorine containing resins such as polytetrafluoroethylene and polytrifluorochloroethylene etc.; utensils or containers made of or provided with linings of rigid polyvinylchloride resin or soft polyvinylchloride resin with a relatively low plasticizer content; and utensils or containers provided with glass linings. In addition, bags or other shapes of utensils made of polyethylene, such as a container arranged inside a drum, may also be employed.

As mentioned in the foregoing, the acrylamide aqueous solution handling method of this invention is applicable to the acrylamide aqueous solutions that are manufactured through the hydration reaction of acrylonitrile carried out using the above stated copper catalysts. The method of the invention, however, is not limited to such and, when so required, may be also effectively applied to general acrylamide aqueous solutions prepared by other processes including, for example, the acrylamide aqueous solution obtained in accordance with the process disclosed by U.S. Pat. No. 3,673,250 which employs homogeneous catalysts comprising organic phosphines and transition metal compounds.

Generally, the concentration of the acrylamide aqueous solution that are chiefly handled in accordance with the method of this invention is normally within a range from 20 to 70% by weight. However, the method of the invention is also applicable to such a case where a solution of a high concentration exceeding 70% by weight is temporarily stored.

EXAMPLE 1

Raney copper which has been developed by a normal method is put in a reactor of 1 liter equipped with a stirrer and a catalyst separator. Following this, the materials from which most of dissolved oxygen has been removed beforehand by a deoxidizing device, i.e. acrylonitrile and water, are continuously supplied to the reactor to allow reaction for 10 days. Furthermore, 40 ppm of methylquinone has been added to the acrylonitrile as stabilizer beforehand while equivalent to 14 ppm of copper nitrate has been added to the water. The approximate composition of the solution obtained through this reaction process is: 15% acrylonitrile, 20% acrylamide and 65% water. This solution is distilled by a vacuum distillation column. Acrylonitrile and water are obtained as distillates while a crude acrylamide aqueous solution is obtained as a bottom. The crude acrylamide aqueous solution thus obtained is passed through a granular active carbon column, and is further passed through a cation exchange resin column. An acrylamide aqueous solution which is obtained through these processes shows a pH value of 3.6, which is then adjusted to pH 5.5 by adding 1N.NaOH thereto. The following table shows the analysis values of the acrylamide aqueous solution obtained as above described:

|  | Analysis values |
|---|---|
| Acrylamide concentration | 33.0% |
| Residual acrylonitrile | 0.02% |
| Residual copper ion | 0.9 ppm |
| Residual methylquinone | Not detected |
| Methanol insoluble matter* | Not detected |
| Hue (APHA) | 5 |
| pH | 5.5 |

Note:
*"Methanol insoluble matter" means a component which separates when 100 ml of methanol is added to 10g of the aqueous solution. If there is an acrylamide polymer, it is normally detectable by this.

Using this acrylamide aqueous solution as testing solution, the materials listed in the following table are subjected to tests. The tests are conducted by placing 200 ml of testing solution in a flask of a capacity of 300 ml equipped with a water cooling condenser. Then each test piece measuring 60 mm in length, 20 mm in width and 3 mm in thickness is immersed in the testing solution. Following this, the flask is immersed in a constant temperature water bath of 50°C. After immersion has continued for 6 days to one month, the variations of the acrylamide aqueous solution and the test piece is examined with the unaided eye. The results are as shown in the following table:

| Materials (Manufacturers) | Period of immersion | Changes of test pieces | Changes of aqueous solution | Remarks |
|---|---|---|---|---|
| Phenol resin coat (A Co. & C Co.) | 32 days | None | None | Good |
| Furan resin FRP (A Co.) | 6 | None | Colored | Bad |
| Epoxy resin coat (A Co.) | 6 | None | Polymerized | Bad |
| Polyester resin FRP, bisphenol (A Co.) | 32 | None | Some color | Bad |
| Neoprene plate (B Co.) | 26 | None | Some color | Bad |
| Natural rubber plate-1 (B Co.) | 32 | None | None | Good |
| Natural rubber plate-2 (B Co.) | 32 | None | Some color | Bad |
| Low-density polyethylene | 36 | None | None | Good |
| High-density polyethylene | 36 | None | None | Good |
| Polypropylene | 36 | None | None | Good |
| Rigid polyvinylchloride resin | 30 | None | None | Good |
| Gun metal plate | 8 | Some discolor | Dark blue (copper elusion) | Bad |
| Copper plate | 8 | Some discolor | Yellowish green (copper elusion) | Bad |
| SUS-27 | 26 | None | None | Good |
| Fluorine-contained resin (tetrafluoroethylene) | 36 | None | None | Good |
| Reference (without test pieces) | 36 | None | None | Good |

EXAMPLE 2

Containers of capacities ranging from 1 to 20 liters and made of materials that attained "good remarks" in Example 1 are used. Each of these containers is filled with the same testing solution as the one employed in Example 1. The container is tightly sealed leaving a space of air equivalent to about 20% of the capacity of the container. In this condition, the container is left for a period 1 to 6 months outdoors in a place exposed to direct rays of the sun. After this, the changes in the internal material and in the acrylamide aqueous solution are examined by observation with the unaided eye and by analysis. The results of the examination are as shown in the following table.

The lining or coating work with resins on the containers made of iron is performed by the people specialized in work for such materials.

| Container material | | Capacity, liter | Test period, month | Container appearance | Test results of testing solution | | | |
|---|---|---|---|---|---|---|---|---|
| Body | Lining or coating | | | | Hue (APHA) | Methanol test* | pH | Turbidity |
| Iron | Phenol resin (A Co.) | 1 | 5 | Normal | 5 | ⊖ | 5.65 | No |
| " | Epoxy resin (A Co.) | 1 | 1 | Normal | 5 | ⊖ | 6.3 | Yes |
| " | Same as above | 1 | 1 | Normal | 5 | ⊕ | 5.75 | No |
| " | Polyester (bisphenol) (A Co.) | 1 | 1 partially peeled | Discolored, | ——————Gelation—————— | | | |
| " | Same as above | 1 | 1 | | 20 | ⊕ | 5.95 | No |
| " | Chlorinated polyethylene (B Co.) | 1 | 1 | Coating material softened | 5 | ⊖ | 6.0 | No |
| " | Same as above | 1 | 1 | Same as above | 5 | ⊕ | 5.65 | No |
| " | Natural rubber (B Co.) | 1 | 1 | Normal | ——————Gelation—————— | | | |
| " | (Nothing) | 1 | 1 day | Discolored, black | ——————Gelation—————— | | | |
| Polyethylene, (low density) | (Nothing) | 20 | 5 | Normal | 5 | ⊖ | 5.65 | No |
| Polypropylene | (Nothing) | 1 | 5 | Normal | 5 | ⊖ | 5.65 | No |
| Rigid polyvinylchloride | (Nothing) | 1 | 5 | Normal | 5 | ⊖ | 5.60 | No |
| Glass | (Nothing) | 10 | 7 | Normal | 5 | ⊖ | 5.5 | No |
| SUS-27 | (Nothing) | 7 | 1 | Normal | 5 | ⊖ | 5.85 | No |
| | | | 2 | " | 5 | ⊕ | 5.55 | No |
| " | (Nothing) | 1 | 1 | Normal | 5 | ⊖ | 5.80 | No |
| | | | 2 | " | ——————Gelation—————— | | | |
| FRP | Polyester (bisphenol) (D Co.) | 1 | 3 | Normal | 5 | ⊖ | 5.7 | No |
| " | Polyester (isophthalic acid) (D Co.) | 1 | 2 | Normal | 5 | ⊖ | 5.65 | No |
| | | | 3 | " | ——————Gelation—————— | | | |
| " | Polyester (isophthalic acid) (D Co.) | 1 | 1 | Normal | 5 | ⊖ | 5.7 | No |
| | | | 2 | " | ——————Gelation—————— | | | |

Note:
*Mark⊕ indicates that, in the methanol test, white turbidity (or precipitate) is produced when 100 ml of methanol is added to 10g of the testing solution. Mark⊖ indicates that the solution remains transparent and no precipitate is produced. Furthermore, mark⊕ means that polymer of acrylamide is produced in the testing solution.

EXAMPLE 3

The materials that give good results in Example 2 above are employed in this example. The same acrylamide aqueous solution as in Example 1 is employed as testing solution. In the same manner as described in Example 1, immersion tests are conducted at a temperature of 50°C for 3 months. Examination is made in the same manner as in Example 2, and the results are as shown in the following table. The table indicates that all of these materials are usable.

| Materials (Manufacturers) | Appearance of test pieces | Test results of testing solution | | | |
|---|---|---|---|---|---|
| | | Hue (APHA) | Methanol test | pH | Turbidity |
| Phenol resin lining (A Co.) | No changes | 5 | — | 5.8 | None |
| High-density polyethylene | No changes | 5 | — | 5.95 | None |
| Polypropylene | No changes | 5 | — | | None |
| Rigid polyvinyl chloride | No changes | 5 | — | 5.59 | None |
| Blank (without test piece) | No changes | 5 | — | 6.05 | None |
| Reference, SUS-27 | No changes | ——————Gelation—————— (7 days) | | | |

EXAMPLE 4

With the same reaction and distillation devices as those of Example 1 arranged, a condenser made of glass is connected to them. Next, a steel tube which has a phenol resin coated lining and measuring 3 cm in inside diameter and 80 cm in length and which is filled with 500 cc of a sulfonic acid type cation exchange resin regenerated with hydrochloric acid is also connected for the purpose of removing a slight amount of metal ion in the crude aqueous solution to be processed. The crude acrylamide aqueous solution obtained through the same reaction and distillation processes as in Example 1 is applied to this arrangement. The temperature of the solution is about 30°C when it comes out from the condenser. The pH value of the solution is about 3.5 after it comes out from the ion exchange resin column and remains unchanged over a period of 6 days.

At first, a stainless steel (SUS-27) pipe measuring 4 mm in inside diameter is connected to the outlet port of the ion exchange resin column to conduct the solution into a reservoir. However, the pipe is often clogged with a sponge-like polymer of acrylamide produced inside the pipe. In view of this frequent trouble, the pipe is replaced with soft polyvinylchloride pipe, polyethylene pipe, polypropylene pipe and glass lining pipe on the second, third and fourth days. Then, there is produced no polymer with each of these replacement pipes used for about 24 hours.

EXAMPLE 5

Tests are conducted on acrylamide aqueous solutions obtained in accordance with various catalytic hydration processes. Each reaction produced solution is subjected to tests after removing non-reacted acrylonitrile as necessary, in the same manner as in Example 1. Then, each solution is refined through a granular active carbon column and a cation exchange column before testing. The catalytic hydration reaction with each catalyst is carried out in the following manner:

Sample 1: A reaction tube made of SUS-27 stainless steel measuring 30 mm in inside diameter and 300 mm in length is filled with 390g (bulk volume: 220 ml) of cupric oxide tablets (manufactured by Nikki Kagaku KK). Then, reduction is carried out at 200° – 270°C by flowing hydrogen gas and nitrogen gas at the rates 200 and 400 ml/min respectively. By this, a reduced copper catalyst of percent reduction of 98%, as determined from the degree of decrease in quantity, is prepared. After this, acrylonitrile and water are continuously supplied to the reaction tube at the rates of 140 and 690 g/hr. respectively to carry out reaction at 120°C. At the same time, the reacting solution is circulated at a rate of 40 liters/hr. An acrylamide aqueous solution obtained through this reaction, wherein the rate of conversion from acrylonitrile to acrylamide is 70%.

Sample 2: A reduced copper-chrome catalyst is prepared in the same manner as in the case of Sample 1 with the exception of that 670g of copper-chrome catalyst tablets (N201 manufactured by Nikki Kagaku KK) is employed. Using this catalyst, hydration reaction is carried out in almost the same manner as in the case of Sample 1 to obtain an acrylamide aqueous solution also at almost the same rate of conversion.

Sample 3: Using a reactor (made of SUS-27 stainless steel) of 1 liter equipped with a stirrer and a catalyst separator, 250g of copper powder is put into the reactor. Then, acrylonitrile and water in which 10g of cupric ion is dissolved are continuously supplied to the reactor at the rates of 140 g/hr and 690 g/hr respectively to carry out reaction at 120°C. The rate of conversion from acrylonitrile to acrylamide is 14%.

Sample 4: A commercially available natrium type ion exchange resin called Amberlite IRC-50 is treated with a cuprous oxide suspension aqueous solution to obtain a cuprous catalyst. Then, using the reactor employed in the case of Sample 3, 200g of acrylonitrile, 300g of water and 100g of the above stated cuprous resin catalyst are put into the reactor to carry out reaction at 120°C for 4 hours in the presence of a slight amount of an antioxidant. The rate of conversion from acrylonitrile to acrylamide is 11%.

Under the same conditions as described in Examples 2 and 3, the acrylamide aqueous solutions obtained in accordance with the above stated processes are subjected to tests by storing them in a container having phenol resin linings, a polyethylene container, a polypropylene container, a rigid polyvinylchloride resin container, an iron container having polytrifluorochloroethylene lining and an iron container having glass lining. The test results are about the same as those of Example 1 wherein tests are conducted on the acrylamide aqueous solution manufactured using Raney copper.

What is claimed is:

1. In a method for handling in storage or transit 20 to 70 wt% acrylamide aqueous solutions obtained by reacting acrylonitrile with water in the presence of a copper catalyst and purifying the resultant crude acrylamide, the improvement consisting of containing said acrylamide aqueous solution which contains no effective amount of polymerization inhibitor in a utensil made of or lined with materials selected from the group consisting of phenol resin, polyethylene, polypropylene, and polyvinylchloride resin, thereby preventing the polymerization of the acrylamide during said storage or transit.

2. The improvement according to claim 1, wherein said acrylamide is one which is obtained by purifying the crude solution with cation exchange resin.

3. The improvement according to claim 1, wherein said solution is one which is obtained by purifying the crude acrylamide by active carbon treatment followed by cation exchange resin treatment and neutralization.

4. The method of claim 1 wherein said copper catalyst is Raney copper, reduced copper, copper-chrome reduced catalyst, copper ion or cuprous resin catalyst.

* * * * *